United States Patent [19]

Kudo et al.

[11] Patent Number: 5,213,102
[45] Date of Patent: May 25, 1993

[54] SHOCK WAVE GENERATING APPARATUS CAPABLE OF SETTING MOVING DIRECTION OF SHOCK WAVE GENERATING SOURCE TO ULTRASONIC TOMOGRAPHIC IMAGE PLANE

[75] Inventors: Nobuki Kudo, Tochigi; Fujio Terai, Kanagawa, both of Japan

[73] Assignee: Kabushiki Kaisha Toshiba, Kawasaki, Japan

[21] Appl. No.: 840,587

[22] Filed: Feb. 26, 1992

Related U.S. Application Data

[63] Continuation of Ser. No. 517,656, May 1, 1990, abandoned.

[30] Foreign Application Priority Data

May 8, 1989 [JP] Japan .................................. 1-113767

[51] Int. Cl.$^5$ .......................... A61B 17/22; A61B 8/13
[52] U.S. Cl. ...................... 128/660.03; 128/024 OEL
[58] Field of Search ......... 128/660.03, 24 EL, 24 AA

[56] References Cited

U.S. PATENT DOCUMENTS

| | | | |
|---|---|---|---|
| 4,669,483 | 6/1987 | Hepp et al. ........................ | 128/660 |
| 4,763,652 | 8/1988 | Brisson et al. ...................... | 128/328 |
| 4,787,394 | 11/1988 | Ogura .............................. | 128/24 EL |
| 4,803,995 | 2/1989 | Ishida et al. ...................... | 128/660.01 |
| 4,821,729 | 4/1989 | Makofski et al. ................. | 128/660.03 |
| 4,821,730 | 4/1989 | Wurster et al. .................. | 128/660.03 |
| 4,917,095 | 4/1990 | Fry et al. .......................... | 128/660.03 |
| 4,928,672 | 5/1990 | Grasser et al. ................... | 128/24 A |
| 4,958,639 | 9/1990 | Uchiyama et al. ............... | 128/660.03 |
| 4,962,754 | 10/1990 | Okazaki ............................ | 128/660.03 |
| 4,984,575 | 1/1991 | Uchiyama et al. ............... | 128/660.03 |
| 4,986,259 | 1/1991 | Aida et al. ......................... | 128/660.03 |
| 4,986,275 | 1/1991 | Ishida et al. ...................... | 128/660.03 |
| 4,991,604 | 2/1991 | Wurster et al. .................. | 128/660.03 |

FOREIGN PATENT DOCUMENTS

| | | |
|---|---|---|
| 0169311 | 1/1986 | European Pat. Off. . |
| 0225104 | 6/1987 | European Pat. Off. . |
| 0269801 | 6/1988 | European Pat. Off. . |
| 0301360 | 2/1989 | European Pat. Off. . |
| 3721187A1 | 1/1980 | Fed. Rep. of Germany . |
| 3826709A1 | 2/1989 | Fed. Rep. of Germany . |
| 2207247 | 1/1989 | United Kingdom ........... 127/24 EL |

OTHER PUBLICATIONS

Edap LT-01 (Jul. 12, 1989).

Primary Examiner—Lee S. Cohen
Assistant Examiner—K. M. Pfaffle
Attorney, Agent, or Firm—Foley & Lardner

[57] ABSTRACT

In a shock wave generating apparatus, a focal point marker is automatically made coincident with an image of an article to be disintegrated on a display screen. The shock wave generating apparatus includes: a shock wave generating source for producing a shock wave and transmitting the shock wave to a biological body under medical examination; an ultrasonic imaging unit including an ultrasonic probe to project an ultrasonic wave beam to the biological body, for producing and displaying an ultrasonic tomographic image of tissue within the biological body; a transporting unit for transporting both the shock wave generating source and ultrasonic probe along the biological body; a calculating unit for calculating a focal point of the shock wave generating from the source based upon a probe position signal derived from the ultrasonic probe, and for displaying the focal point within the tomographic image as the focal point marker; and, a transport controlling unit for detecting a positional condition of the ultrasonic probe to output a positional condition signal when an image of an article to be disintegrated located within the tissue of the biological body is displayed on the tomographic image, and for controlling the transporting unit so as to transport both the shock wave generating source and ultrasonic probe along a tomographic image coordinate system defined by the ultrasonic probe based upon the positional condition signal, whereby the focal point marker is continuously coincident with the image of the article to be disintegrated.

10 Claims, 7 Drawing Sheets

SHOCK WAVE GENERATING APPARATUS CAPABLE OF SETTING MOVING DIRECTION OF SHOCK WAVE GENERATING SOURCE TO ULTRASONIC TOMOGRAPHIC IMAGE PLANE

This application is a continuation of application Ser. No. 07/517,656, filed May 1, 1990, now abandoned.

BACKGROUND OF THE INVENTION

1. Field of the Invention

The present invention generally relates to a shock wave generating apparatus capable of disintegrating an article, e.g., cancer cell, and a concretion within a biological object under medical examination, by utilizing focused energy of shock waves. More specifically, the present invention is directed to a shock wave generating apparatus capable of setting a movement direction for a shock wave generating source for its focus to be within an ultrasonic tomographic image plane formed by an ultrasonic probe.

2. Description of the Related Art

Various types of shock wave generating apparatuses have been proposed in, for instance, Japanese KOKAI (Disclosure) patent application No. 62-49843 (1987).

In FIG. 1, there is shown, as a sectional view, an ultrasonic wave applicator 1 of one conventional shock wave generating apparatus.

The construction of this ultrasonic wave applicator 1 is as follows. A through hole having a predetermined shape is formed in a center portion of this applicator 1. A vibrating element (e.g., piezoelectric transducer element) 2 is spherically formed and backing material 3 is uniformly adhered to a rear surface of this spherical vibrating element 2. An imaging ultrasonic probe 4 is positioned in such a manner that a transmitting/receiving wave front (ultrasonic array) 4a is located at the curved surface identical to the shock wave transmitting/receiving wave front of the vibrating element 2, or at the rear side of the transducer for the, last-mentioned wave front. Furthermore, this ultrasonic wave applicator 1 includes a water bag 5 containing water as a coupling medium for the ultrasonic wave. Reference numeral 6 indicates a biological body under medical examination.

Referring now to FIGS. 2 and 3A to 3D, a description will be provided for a means for identifying a position of an article to be disintegrated, e.g., a concretion or calculus positioned within the biological body 6 by employment of the above-described conventional ultrasonic applicator 1 shown in FIG. 1. That is to say, this implies a means for discovering the actual position of the concretion within the biological body 6 and for making the focal point of the shock wave coincident with the actual concretion position. As shown in FIG. 2, the conventional ultrasonic applicator 1 supported on a supporting member 7 is moved within an X-Y plane over the biological body 6 mounted on a couch 8. This moving operation is controlled by a joy stick 9. A sector-formed ultrasonic beam is projected from the ultrasonic probe 4 employed within the applicator 1, so that a B-mode ultrasonic image (i.e., slice image) of the biological body 6 is formed in the known ultrasonic image forming method and then displayed on a television (TV) monitor 10.

An operator manipulates a joy stick 9 while observing the CT image or B-mode tomographic image displayed on the TV monitor 10. For instance, FIG. 3A represents a screen of the TV monitor 10, on which no concretion to be disintegrated within the biological body 6 is discovered, or appears. When the ultrasonic probe 4 is moved by the operator and the concretion is captured by the ultrasonic probe 4, an image 11 of the concretion is displayed on the TV monitor 10 as shown in FIG. 3B. Subsequently, as represented in FIG. 3C, the ultrasonic applicator 1 is moved in such a manner that the image 11 of the concretion to be disintegrated is positioned at a center of the screen on which a marker 12 to indicate a focal point of a shock wave is also displayed. Then, as shown in FIG. 3D, the ultrasonic applicator 1 is moved downwardly in such a way that the concretion image 11 is moved toward a higher direction of the TV monitor 10 so as to be coincident with the position of the focal point marker 12. As a result, the position of the concretion within the biological body 6 may be identified by the focal point of the shock wave.

As apparent from the foregoing, since the conventional means for identifying the article to be disintegrated is used for the ultrasonic diagnostic apparatus as an imaging means for tissue within a biological body, such an ultrasonic identifying means has a particular advantage in that, for instance, a gallstone mainly containing cholesterol, and soft tissue can be visualized, as compared with the use of X-ray diagnostic apparatus. However, ultrasonic diagnostic apparatus functioning as concretion identifying means has the following drawbacks. That is, since generally, an ultrasonic diagnostic apparatus is for obtaining a two-dimensional CT image of a biological body parallel to an array direction of transducer elements just under an ultrasonic probe, it is rather difficult to identify a position of an article to be disintegrated, as compared with an X-ray diagnostic apparatus for convoluting three-dimensional images along a depth direction of the biological body so as to acquire a two-dimensional image.

That is to say, an article to be disintegrated is continuously displayed on a TV monitor of an X-ray diagnostic (fluoroscopic) apparatus when this article is present within a field of view, whereas an article to be disintegrated is displayed on a TV monitor of an ultrasonic diagnostic apparatus only when this article is positioned on a tomographic image plane (slice plane) produced by way of an ultrasonic probe. As a consequence, in case an article to be disintegrated is discovered from a slice plane produced by way of an ultrasonic probe by an operator and then an image of this article is in coincidence with a focal point marker of a disintegrating shock wave displayed on a monitor screen, this article's image may disappear from the monitor screen of the ultrasonic diagnostic apparatus unless a source of an ultrasonic shock wave is moved along a direction coincident with the above-described slice plane. Under these circumstances, the conventional identifying operation for the position of the article to be disintegrated becomes very difficult, because the shock wave generating source must be transported in such a manner that the article to be disintegrated never disappears from the ultrasonic slice image produced by way of the ultrasonic probe.

The present invention has been made in an attempt to solve the above-described problems and therefore has the object of providing a shock wave generating apparatus capable of simply identifying a position of an article to be disintegrated on a ultrasonic slice plane displayed on a monitor screen. More specifically, another object of the present invention is to provide such a shock wave generating apparatus that when a focal point of a shock wave generating source is made coincident with an image of an article to be disintegrated on a monitor screen of an ultrasonic diagnostic apparatus after the image of this article has been displayed on this monitor screen, a movement (transport) direction for the generating source can be automatically for its focus to be within the tomographic image plane of the ultrasonic probe.

SUMMARY OF THE INVENTION

To achieve the above-described objects, a shock wave generating apparatus according to the present invention, comprises:

source means (21) for producing a shock wave and transmitting the shock wave to a biological body under medical examination;

ultrasonic imaging means (200) including ultrasonic probe means (22;30) to project an ultrasonic wave beam to the biological body, for producing and displaying an ultrasonic tomographic image of tissue within the biological body;

transporting means (34) for transporting both the shock wave generating source means (21) and the ultrasonic probe means (22) along the biological body;

calculating means (30;31) for calculating a focal point of the shock wave generated from the source means (21) based upon a probe position signal derived from the ultrasonic probe means (22), and for displaying the focal point as a focal point marker (32); and transport controlling means (35;36;37;38) for detecting a positional condition of the ultrasonic probe means (22) to output a positional condition signal when an image (40) of an article to be disintegrated located within the tissue of the biological body is displayed on the tomographic image, and for controlling the transporting means (34) so as to transport both the shock wave generating source means (21) and the ultrasonic probe means (22) along a tomographic image coordinate system (Xp, Yp, Zp) defined by the ultrasonic probe means (22) based upon the positional condition signal, whereby the focal point marker (32) is coincident with the image (40) of the article to be disintegrated.

BRIEF DESCRIPTION OF THE DRAWINGS

For a better understanding of the present invention, reference is made to the following description in conjunction with the accompanying drawings, in which.

DETAILED DESCRIPTION OF THE PREFERRED EMBODIMENTS

Overall Arrangement of First Shock Wave Generating Apparatus

Figure 1:
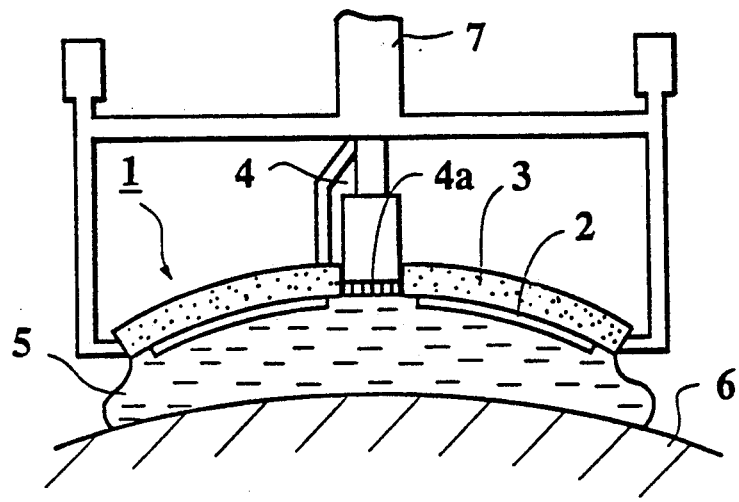
FIG. 1 is a sectional view of an ultrasonic pulse applicator employed in a conventional shock wave generating apparatus.
Figure 2:
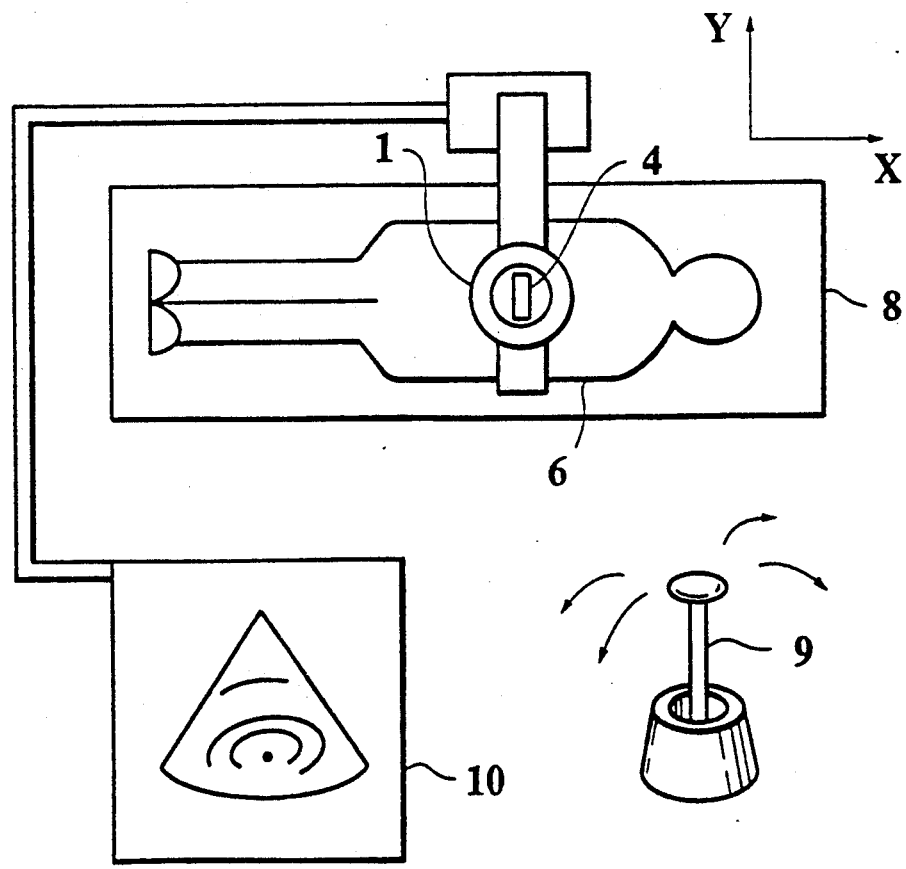
FIG. 2 is an illustration for schematically explaining operations of the conventional shock wave generating apparatus employing the ultrasonic pulse applicator shown in FIG. 1.
Figure 3A:
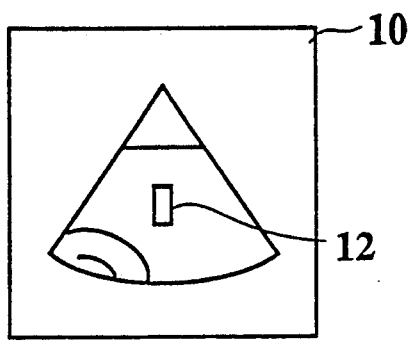
FIGS. 3A to 3D are illustrations for explaining a conventional identifying operation for an article to be disintegrated in an ultrasonic tomographic image.
Figure 3B:
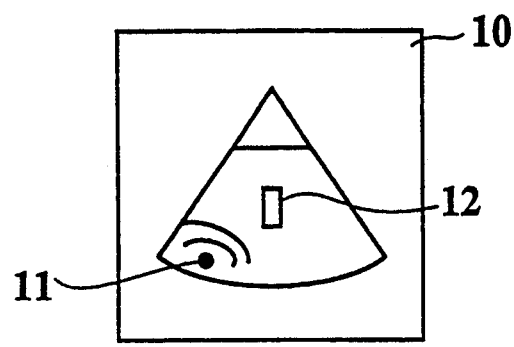
Figure 3C:
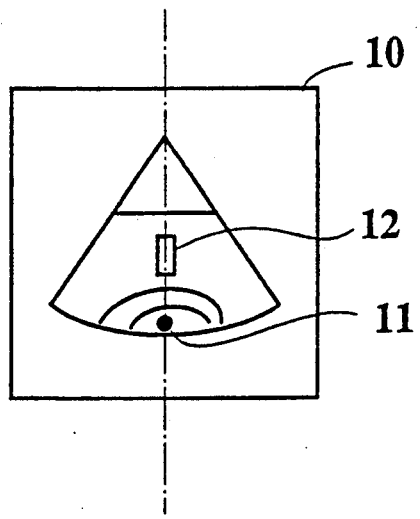
Figure 3D:
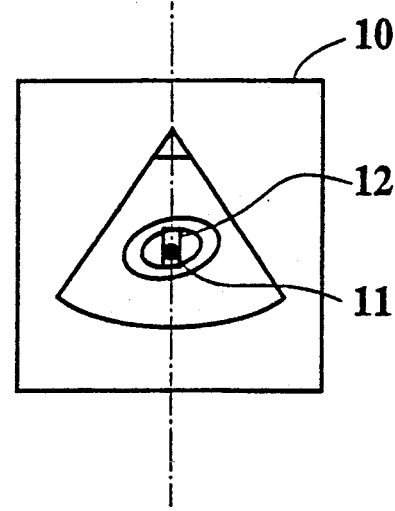
Figure 4:
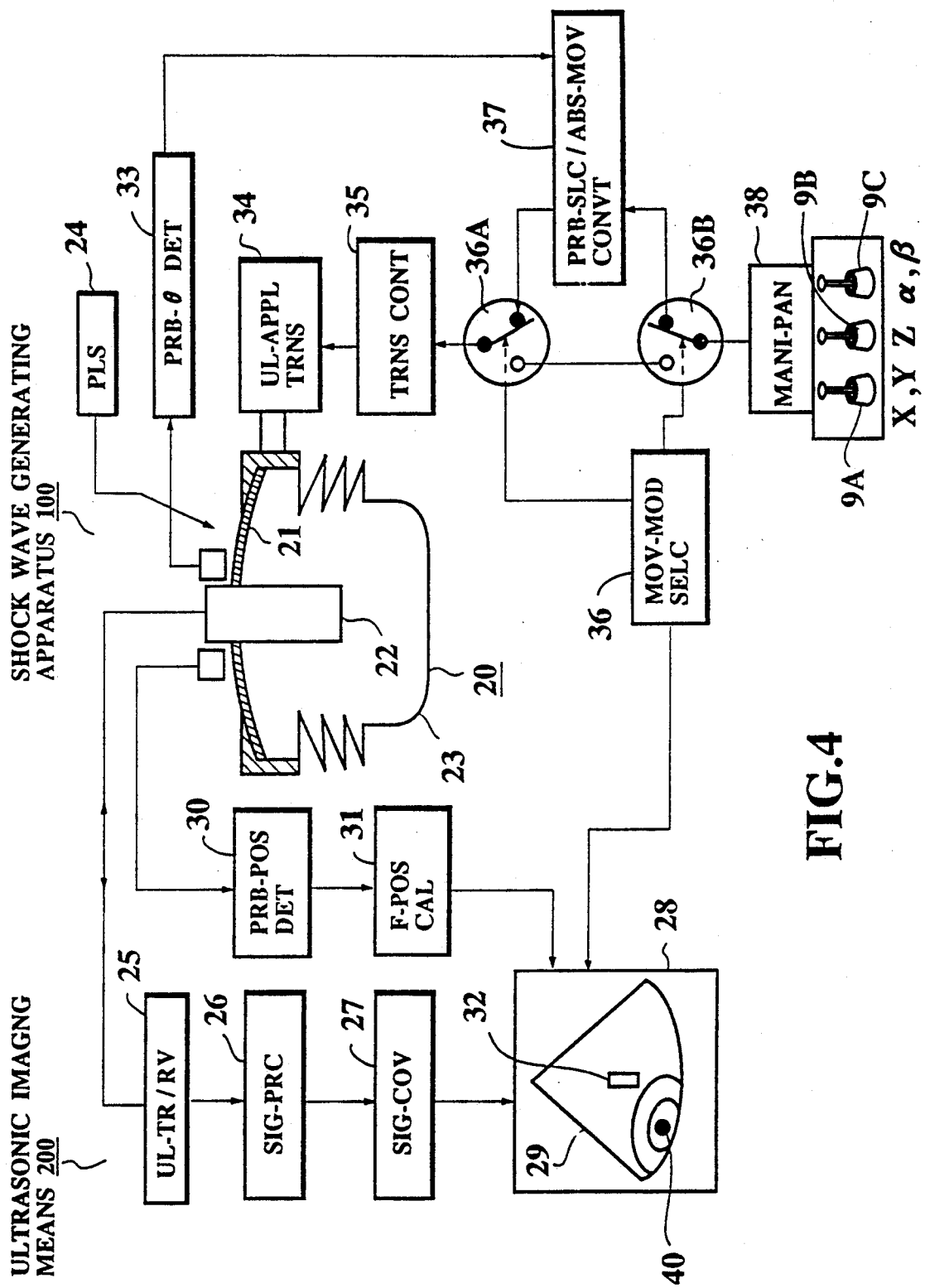
FIG. 4 is a schematic block diagram of an arrangement of a shock wave generating apparatus 100 according to a first preferred embodiment of the present invention.

Referring now to FIG. 4, an overall arrangement of a shock wave generating apparatus 100 according to a first preferred embodiment of the present invention, in conjunction with an ultrasonic imaging apparatus 200, will be described.

As is apparent from the arrangement shown in FIG. 4, the first preferred embodiment of the shock wave generating apparatus 100 utilizes an ultrasonic wave as a shock wave.

An ultrasonic (wave) applicator 20 is employed in the shock wave generating apparatus 100 and is so designed as to be freely transported in various directions along a biological body (not shown in detail) under medical examination by a transport mechanism (as will be discussed later). A shock wave transducer 21 having a concave surface, as viewed in a sectional plane thereof, is provided on a rear surface of this ultrasonic applicator 20 so as to produce therefrom an ultrasonic wave as a shock wave. Furthermore, an ultrasonic (wave) probe 22 of an ultrasonic imaging apparatus 200 is provided at a central portion of the concave surface of the shock wave transducer 21. Reference numeral 23 indicates a water bag.

A pulser (PLS) 24 is employed to transmit a pulsatory excitation signal to the shock wave transducer 21. An ultrasonic transmitting/receiving circuit (UL-TR/RV) 25 is connected to the ultrasonic probe 22 so as to send another pulse signal thereto for sector scanning excitation. Thus, the transmitting/receiving circuit 25 transmits the ultrasonic wave beam to the biological body under medical examination and receives an echo pulse therefrom. A signal processing circuit (SIG-PRC) 26 is connected to the transmitting/receiving circuit 25 so as to amplitude-detect an output signal therefrom. A signal converting circuit (SIG-COV) 27 is connected to the signal processing circuit 26, whereby an output signal from the signal processing circuit 26 is converted into a corresponding video signal. This video signal is supplied to a display unit 28, e.g., a television monitor so that a sector (B-mode)tomographic image 29 is displayed on the display unit 28. A probe position detecting unit (PRB-POS DET) 30 is further employed to detect a dimension (distance) of the ultrasonic probe 22 along a depth direction thereof, as inserted into the ultrasonic applicator 20. A focal point calculation unit (F-POS CAL) 31 is connected to the probe position detecting unit 30 in order to calculate a focal point of a shock wave from a shock wave generating source, i.e., the ultrasonic shock wave transducer 21, on the monitor screen of the display unit 28. The calculated focal point from the focal point calculating unit 31 is displayed as a focal point marker 32 at a corresponding marker position on the monitor screen.

A probe rotation angle detecting unit (PRB-$\theta$ DET) 33 is further employed so as to detect a present tomographic (slice) plane direction of the ultrasonic probe 22, namely a rotation angle of the ultrasonic probe 22. To cause coincidence between a position of the shock wave generating source and an article to be disintegrated, an applicator moving mechanism (UL-APPL TRNS) 34 for mechanically moving the ultrasonic applicator 20 in various directions (as will be described in detail) provided. This applicator moving mechanism 34 is controlled by a transport mechanism control unit 35, so that the ultrasonic applicator 20 is transported along various directions X, Y, Z in a three-dimensional coordinate system, in an $\alpha$ (alpha) direction (i.e., a rotation direction around the X axis), and a $\beta$ (beta) direction (i.e., a rotation direction around the Y axis).

Reference numeral 36 indicates a transport control mode selecting switch (MOV-MOD SELC) 36 for selecting a transport control mode for the ultrasonic applicator 20 between an absolute coordinate system transport control mode and a probe slice plane (probe movement coordinate system) transport control mode. When the probe slice plane transport control mode is selected by operating this selecting switch 36, transport control information on the probe slice plane must be converted into transport information on the absolute coordinate system. To this end, a probe slice plane/absolute coordinate transport direction converting unit (PRB-SLC/ABS-MOV CONVT) 37 is employed and connected to the transport mode selecting switch 36 and probe rotation angle detecting unit 33. An operation panel (MANI-PAN) 38 on which three joy sticks are mounted is employed so as to input various transport control information into the transport mechanism control unit 35. It should be noted that the transport control mode which has been selected by the selecting switch 36 is displayed on the monitor screen of the display unit 28.

Coordinate System Converting Method

A description will now be provided for a major feature of the present invention, i.e., a converting method for performing conversion between a probe slice plane transport control mode and an absolute coordinate system transport control mode.

Figure 5A:
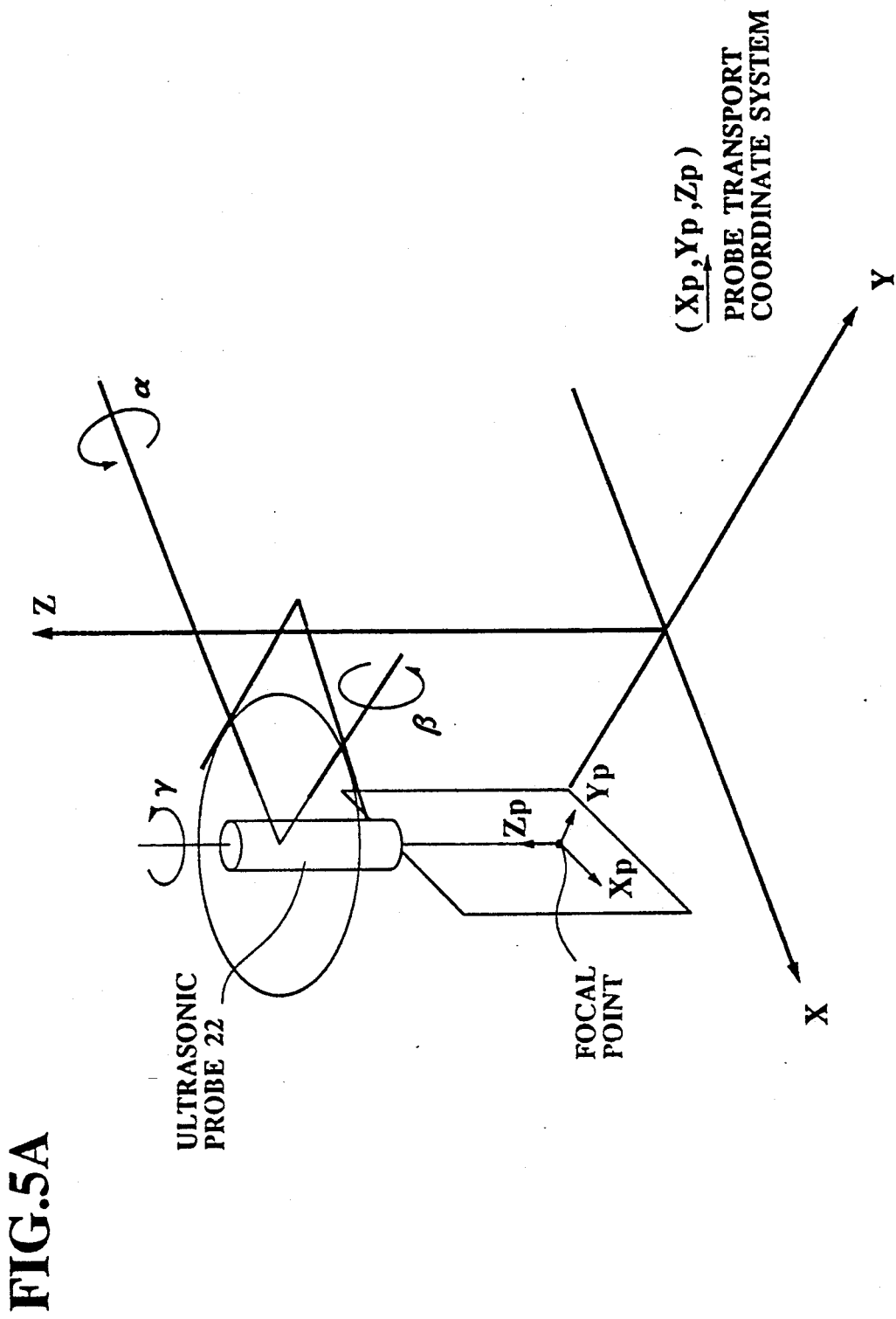
FIGS. 5A and 5B are illustrations for schematically representing a probe coordinate system and a coordinate conversion between the ultrasonic coordinate system and an absolute coordinate system.

In FIG. 5A, there is shown an illustration of a relationship between the absolute coordinate system (X, Y, Z) and the probe movement coordinate system (Xp, Yp, Zp). As apparent from FIG. 5A, the probe movement coordinate system corresponds to such a coordinate system as is rotated around the X, Y, and Z axes by $\alpha$, $\beta$, and $\gamma$ directions. The actual moving directions of the ultrasonic applicator 20 are illustrated by arrows in FIG. 6.

Figure 5B:
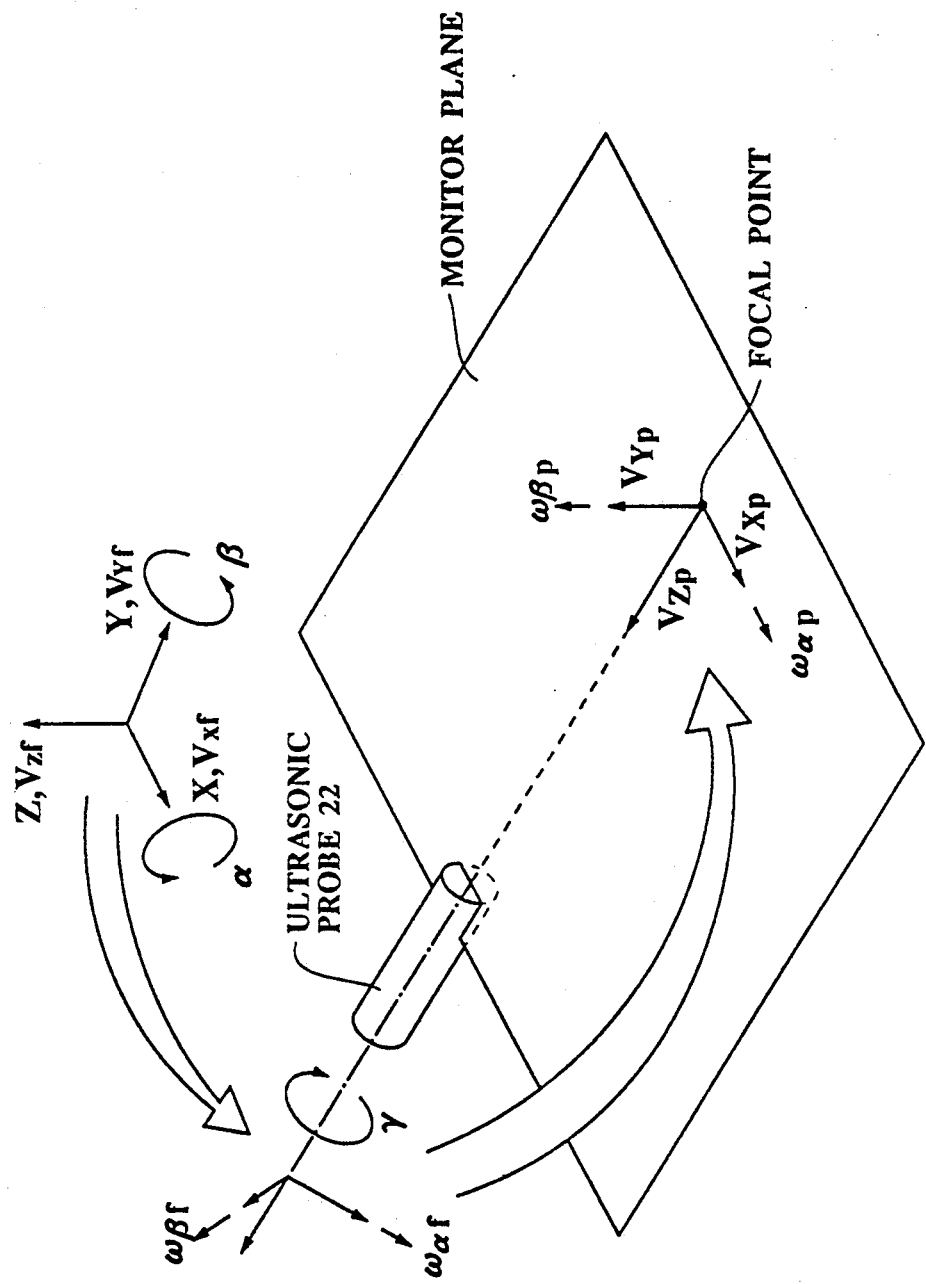

Furthermore, FIG. 5B illustrates the coordinate system conversion when the probe transport control mode is selected.

A detailed coordinate system conversion will be described later.

Overall Operation

Referring now to FIGS. 4 through 5, the overall operation of the shock wave generating apparatus 100 will be described.

As previously stated, the ultrasonic applicator 20 is mainly constructed of the probe position detecting unit 30 for detecting the positional relationship between this applicator 20 and ultrasonic probe 22, and also the probe rotation angle detecting unit 33 for detecting the probe rotation angle with respect to the ultrasonic applicator 20. The positional signal derived from the probe position detecting unit 30 is supplied to the focal point calculating unit 31 in which the focal point of the ultrasonic shock wave is calculated with respect to the monitor screen area shown by the display unit 28. The resultant focal point is displayed as the focal point marker 32 on this monitor screen.

Focusing Article To Be Disintegrated

Figure 6:
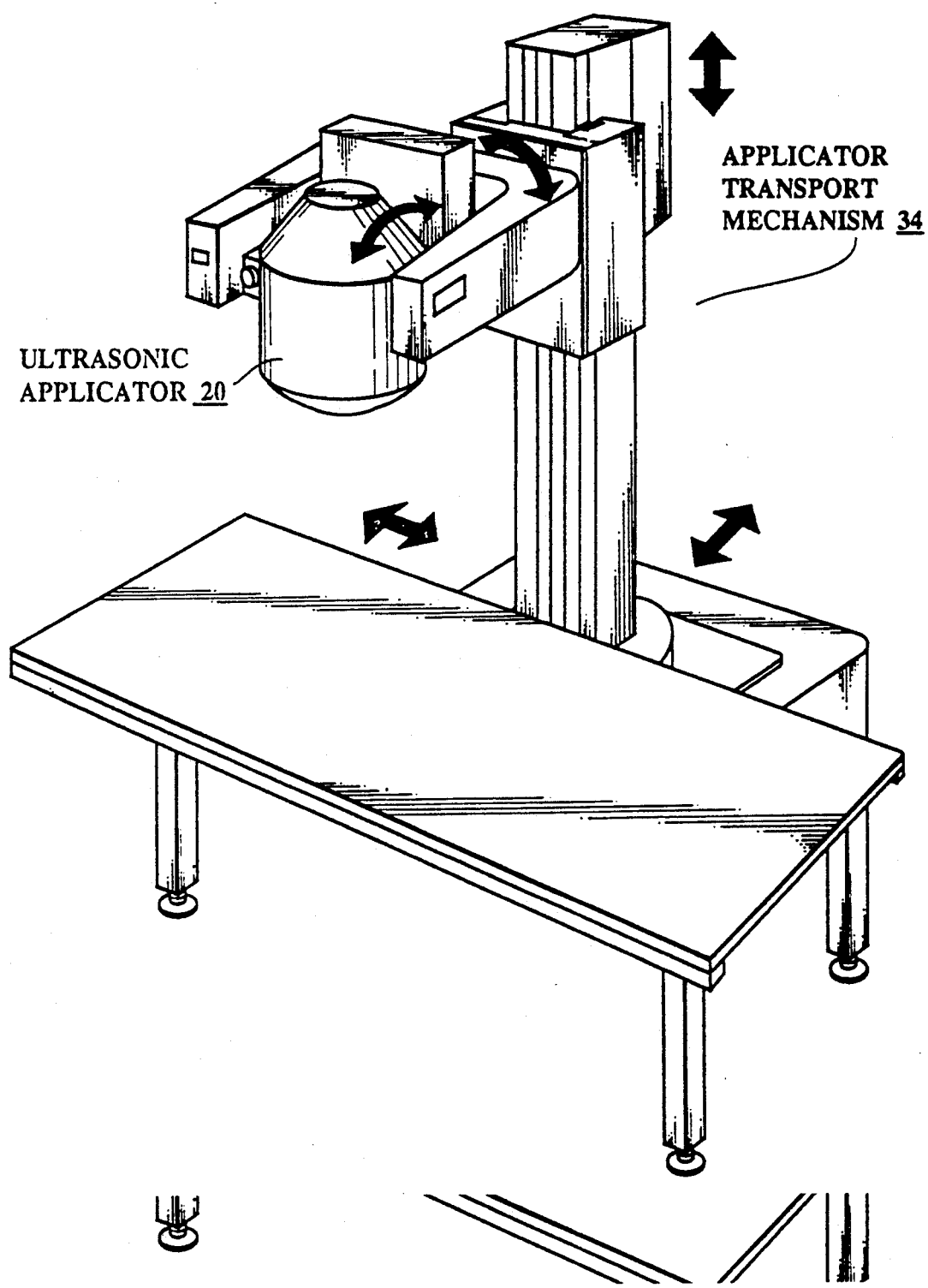
FIG. 6 is a perspective view of the first shock wave generating apparatus 100 shown in FIG. 4; and, FIG. 7 is a schematic block diagram of the internal circuits of the major arrangements 34, 35, 37 employed in the first shock wave generating apparatus 100 shown in FIG. 1.

To focus the ultrasonic shock wave onto an article to be disintegrated (i.e., an image 40), the applicator transport control mechanism 34 controls the movement of the ultrasonic applicator 20 in accordance with the following transport control modes. As previously described, there are introduced two transport control modes for this applicator 20. In the first transport control mode, the applicator 20 is transported in parallel to, or rotated around the absolute coordinate system which is determined by the actual construction of the first shock wave generating apparatus 100, as represented in FIGS. 5A and 6. Further, in the second transport control mode, assuming now that the slice plane of the ultrasonic probe 22, i.e., scanning direction is used as a reference, the applicator 20 is transported in parallel to, or rotated around an axial direction positioned parallel to or perpendicular to this reference plane, as represented in FIG. 5B.

These two transport control modes may be selected by operating the transport control mode selecting switch 36. In the first preferred embodiment, when the probe slice plane transport control mode is selected, this selected control mode is displayed on the monitor screen of the display unit 28. Then, various instructions, e.g., X, Y, Z, $\alpha$ and $\beta$ given by the joy sticks of the operation panel 38 are first supplied to the probe slice plane/absolute coordinate transport direction converting unit 37. As a result, based upon the probe rotation angle information derived from the probe rotation angle detecting unit 33, the above-described probe slice plane transport control data are converted into the absolute coordinate system transport control data which will be then furnished to the transport mechanism control unit 35.

Coordinate System Conversion

The coordinate system conversion between the probe movement coordinate system determined by the ultrasonic tomographic image (slice image) and the absolute coordinate system determined by the construction of the shock wave generating apparatus 100, is another major feature of the present invention. Then, one of the typical coordinate system conversion methods according to the present invention will now be described in detail.

In the absolute transport control mode selected by the transport control mode selecting switch 36 shown in FIG. 4, the various operation instructions given by the joy sticks 9A to 9C are directly applied via switch contacts 36A and 36B of the selecting switch 36 to the transport mechanism control unit 35. As a result, the ultrasonic applicator 20, i.e., ultrasonic probe 22 and shock wave generating source 21 is moved along the 3-dimensional axes X, Y and Z of the absolute coordinate system by the applicator transport mechanism 34 under the control of the transport mechanism control unit 35.

In contrast, when the probe slice plane transport control mode is selected by the selecting switch 36, the various operation instructions within the probe slice plane given by the joy sticks 9A to 9C are first converted into the transport control data for the absolute coordinate system by the probe slice plane/absolute coordinate transport direction converting unit 37 and thereafter the resultant transport control data are supplied via the contact 36A to the transport mechanism control unit 35. Then, similarly, the ultrasonic applicator 20 is moved along the three-dimensional axes X, Y, and Z of the absolute coordinate system by the applicator transport mechanism 34 under the control of the transport mechanism control unit 35. It should be noted that three-dimensional axes Xp, Yp, Zp are defined by the probe transport coordinate system.

In the first preferred embodiment, since there is such a positional relationship with respect to the movement of the ultrasonic applicator 20, as represented in FIG. 5A, the transport instruction signals provided by the joy sticks 9A to 9C are converted by the probe slice plane/absolute coordinate transport direction converting unit 37.

The following operation velocity instructions are inputted by the joy sticks: $V_X$, $V_Y$, $V_Z$, $\omega_\alpha$ and $\omega_\beta$.

When the absolute coordinate transport control mode is selected, $$\begin{bmatrix} V_{Xf} \\ V_{Yf} \\ V_{Zf} \\ \omega_\alpha f \\ \omega_\beta f \end{bmatrix} = \begin{bmatrix} V_{Xf} \\ V_{Yf} \\ V_{Zf} \\ \omega_\alpha f \\ \omega_\beta f \end{bmatrix} \quad (1)$$

Note that a superscript "f" indicates a gradient of a relevant joy stick which has been inputted in the absolute coordinate transport control mode.

When the probe slice plane transport control mode is selected, the following coordinate system conversion is carried out by utilizing the illustration shown in FIG. 5B:

$$\begin{bmatrix} V_{Xf} \\ V_{Yf} \\ V_{Zf} \end{bmatrix} = \begin{bmatrix} \cos\gamma & -\sin\alpha & 0 \\ \sin\gamma & \cos\gamma & 0 \\ 0 & 0 & 1 \end{bmatrix} \begin{bmatrix} \cos\beta & 0 & \sin\beta \\ 0 & 1 & 0 \\ -\sin\beta & 0 & \cos\beta \end{bmatrix} \begin{bmatrix} 1 & 0 & 0 \\ 0 & \cos\alpha & -\sin\alpha \\ 0 & \sin\alpha & \cos\alpha \end{bmatrix} \begin{bmatrix} V_{Xp} \\ V_{Yp} \\ V_{Zp} \end{bmatrix} \quad (2)$$

$$\begin{bmatrix} \omega_\alpha f \\ \omega_\alpha f \end{bmatrix} = \begin{bmatrix} \cos\gamma & -\sin\gamma \\ \sin\gamma & \cos\gamma \end{bmatrix} \begin{bmatrix} \omega_{\alpha p} \\ \omega_{\beta p} \end{bmatrix}$$

Note that a superscript "p" denotes a gradient of a relevant joy stick which has been inputted in the probe slice plane transport control mode.

Matrixes "$P_f$" and "$P_p$" to execute these coordinate conversions are so-called:

$P_f$ - (absolute coordinate transport)
$P_p$ - (probe slice plane transport)

In the first shock wave generating apparatus 100 shown in FIG. 4, when the probe slice plane transport control mode is selected by operating the transport control mode selecting switch 36, the operation instruction velocities given by the corresponding joy sticks 9A to 9C are converted into the required absolute coordinate transport control mode data by utilizing the above-described matrixes $P_f$ and $P_p$, which are then supplied to the transport mechanism control unit 35.

Figure 7:
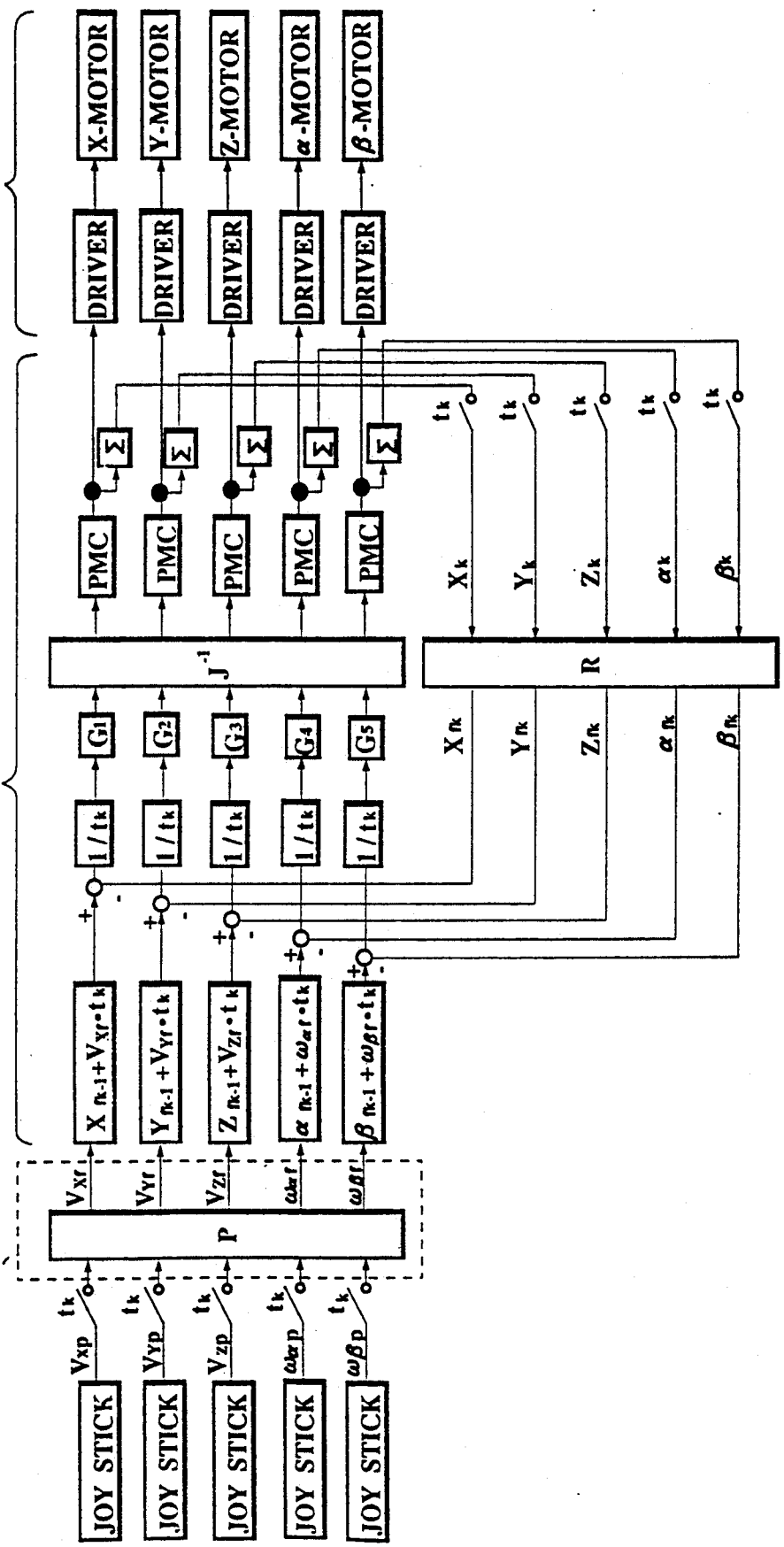

Practical Circuit Arrangement of Major Arrangement of First Shock Wave Generating Apparatus In FIG. 7, there is shown a practical circuit arrangement for the applicator transport mechanism 34, transport mechanism control unit 35, and probe slice plane/absolute coordinate transport converting unit 37 functioning as the major featured arrangement of the first shock wave generating apparatus 100 shown in FIG. 4.

This practical circuit arrangement will now be summarized. The joy stick 9 inputs the various operation instructions, i.e., velocities of $V_{Xp}$, $V_{Yp}$, and $V_{Zp}$, and rotation angles of $\omega_{\alpha p}$ and $\omega_{\beta p}$ into the probe slice plane/absolute coordinate transport converting unit 37 in which the above-described converting matrixes $P_f$ and $P_p$ are calculated. The converted absolute coordinate transport control data of $V_{xf}$, $V_{yf}$, $V_{zf}$, $\omega_{\alpha f}$ and $\omega_{\beta f}$ are furnished to the transport mechanism control unit 35 which is constructed of, for instance, gain controllers $G_1$ to $G_5$, pulse motor controllers, and counters $\Sigma$. The applicator transport controlling data from the transport mechanism control unit 35 are supplied to the applicator transport mechanism 34 which is constructed of drivers, and X, Y, Z-axis motors and also $\alpha$, $\beta$-axis motors.

As is apparent from the circuit arrangement of FIG. 7, a feedback path is constructed in the transport mechanism control unit 35 in order to reduce the difference occurring between the transport instructions provided by the joy sticks and the actual transport.

A symbol "$J^{-1}$" for the transport mechanism control unit 35 indicates Jacobian's inverse matrix. This inverse matrix defers with each other depending upon the absolute transport control mode and probe slice plane transport control mode, and therefore is expressed by the following two matrixes, i.e., "$J^{-1}f$" and "$J^{-1}p$".

$$J^{-1}f = \begin{bmatrix} 1 & 0 & 0 & 0 & 0 \\ 0 & 1 & 0 & 0 & 0 \\ 0 & 0 & 1 & 0 & 0 \\ 0 & 0 & 0 & 1 & 0 \\ 0 & 0 & 0 & 0 & 1 \end{bmatrix} = E \text{ (unit matrix), and}$$

$$J^{-1}p = \begin{bmatrix} 1 & 0 & 0 & 0 & Z_f\cos\beta \\ 0 & 1 & 0 & -Z_f\cos\alpha\cos\beta & Z_f\sin\alpha\sin\beta \\ 0 & 0 & 1 & -Z_f\sin\alpha\cos\beta & -Z_f\cos\alpha\sin\beta \\ 0 & 0 & 0 & 1 & 0 \\ 0 & 0 & 0 & 0 & 1 \end{bmatrix}$$

Furthermore, the symbol "R" for the transport mechanism control unit 35 represents such a calculation. That is, the present position of the ultrasonic applicator 20 is calculated from the motor transporting amounts of the respective axes, and then is given by the following formula:

$$\begin{bmatrix} X_f \\ Y_f \\ Z_f \\ \alpha_f \\ \beta_f \end{bmatrix} = \begin{bmatrix} X - Z_f \sin\beta \\ Y + Z_f \sin\alpha\cos\beta \\ Z - Z_f \cos\alpha\cos\beta \\ \alpha \\ \beta \end{bmatrix}$$

It should be noted that this present position calculation is commonly utilized for both transport control modes.

Referring back to the circuit arrangement to FIG. 4, the applicator transport mechanism 35 is operated in the absolute transport control mode during the actual operation, taking account of body attitudes of a patient (biological body) and positions of various organs. As a result, an image 40 of the article to be disintegrated is displayed in the tomographic (slice) image 29 of the patient on the display unit 28. Subsequently, this absolute coordinate transport control mode is changed into the probe slice plane transport control mode by operating the transport control mode selecting switch 36 so as to make both the image 40 of the article to be disintegrated and the focal point marker 32 of the shock wave generating source 21 coincident. Thereafter, even when an operator manipulates the operation panel 38 so as to input various movement data, e.g., X, Z, α for the transportation of the ultrasonic applicator 20, the image 40 of the article to be disintegrated does not disappear from the monitor screen of the display unit 28, because the movements of the applicator 20 are controlled by the transport mechanism control unit 35 into which these input movement data have been converted into the probe slice plane transport control data and then are supplied. Moreover, even if the image 40 of the article to be disintegrated disappears due to some accidental phenomena, for instance, a movement of a patient, the transport control data Y and β are supplied to converting unit 37 so that the applicator 20 may be transported in a direction perpendicular to the slice plane so as to again display this image 40 on the monitor screen, since the article to be disintegrated most probably exists in slice planes adjacent to the above-described slice plane from which the image 40 of the article to be disintegrated has just disappeared.

As apparent from the foregoing, the present invention is not limited to the above-described first preferred embodiment, but may be modified without departing from the technical scope of the present invention. For instance, the probe rotation angle detecting unit may be realized by combining a gear and a potentiometer.

As previously described in detail, in accordance with the shock wave generating apparatus of the present invention, since when the image of the article to be disintegrated is displayed in the tomographic image produced by the ultrasonic probe 22, this condition is sensed and thereafter both the shock wave generating source and ultrasonic probe are transported along the slice plane (tomographic image), the image of the article to be disintegrated can be continuously displayed within the slice plane while moving the shock wave generating source and ultrasonic probe. In other words, since the moving direction of the applicator can be automatically determined by the probe slice plane/absolute coordinate transport direction converting unit, the article's image never disappears from the display screen. As a consequence, the identifying operations for positioning the article to be disintegrated can be very simply and readily performed.

What is claimed is:

1. A shock wave generating apparatus comprising:
    source means for producing a shock wave and transmitting said shock wave to a biological body under medical examination;
    ultrasonic imaging means, including ultrasonic probe means to project an ultrasonic wave beam to said biological body, for producing and displaying an ultrasonic tomographic image of tissue within said biological body;
    probe position detecting means for detecting a slice plane position of said ultrasonic probe means with respect to said shock wave so as to produce a slice plane positioning signal for said ultrasonic probe means while an image of an article to be disintegrated located within said tissue of said biological body is being displayed in said ultrasonic tomographic image;
    transporting means for transporting both said source means and said ultrasonic probe means;
    generating means for generating a marker indicative of a focal point of said shock wave produced from said source means; and
    transport controlling means for controlling said transporting means so as to transport both said source means and said ultrasonic probe means along a detected slice plane of said ultrasonic probe means in response to said slice-plane positioning signal, whereby said marker is automatically coincident with said image of said article to be disintegrated.

2. A shock wave generating apparatus as claimed in claim 1, wherein said transport controlling means includes
    transport control mode instruction means for instructing one of an absolute coordinate transport control mode and an ultrasonic slice plane transport control mode;
    transport control mode selecting switch means for selecting said absolute coordinate transport control mode or said ultrasonic slice plane transport control mode;
    transport mode converting means for converting said ultrasonic slice plane transport control mode into a corresponding converted absolute coordinate transport control mode when said ultrasonic slice plane transport control mode is selected by said transport control mode selecting switch means; and
    transport mechanism controlling means for controlling said transporting means in response to one of said absolute coordinate transport control mode and said converted absolute coordinate transport control mode, whereby said marker is made coincident with said image of said article to be disintegrated even when said ultrasonic slice plane transport control mode is selected.

3. A shock wave generating apparatus as claimed in claim 2, wherein said transport control mode instruction means comprises an operation panel having a joy stick, and said transport control mode selecting switch means.

4. A shock wave generating apparatus as claimed in claim 2, wherein said transport mechanism controlling means controls said transporting means so as to transport both said source means and said ultrasonic probe means along a three-dimensional coordinate system defining at least an absolute coordinate system.

5. A shock wave generating apparatus as claimed in claim 2, wherein said transport mode converting means converts said ultrasonic slice plane transport control mode into said corresponding converted absolute coordinate transport control mode by utilizing a predetermined matrix.

6. A shock wave generating apparatus as claimed in claim 2, further comprising:

probe rotation angle detector means for detecting a rotation angle of said ultrasonic probe means to produce actual rotation angle data.

7. A shock wave generating apparatus as claimed in claim 6, wherein said transport control mode instruction means inputs velocity data and desirable rotation angle data for said transporting means into said transport mode converting means, whereby coordinate conversion is performed therein based upon said inputted velocity data and said desirable rotation angle data with reference to said actual rotation angle data.

8. A shock wave generating apparatus as claimed in claim 1, wherein said transporting means includes three-dimensional axes motors and two rotation-angle motors.

9. A shock wave generating apparatus as claimed in claim 1, wherein said source means is an ultrasonic transducer.

10. A shock wave generating apparatus as claimed in claim 1, wherein said ultrasonic probe means comprises an ultrasonic probe and wherein said apparatus further comprises; and, probe relative position detector means for detecting a relative position between said ultrasonic probe and said source means so as to produce a positional condition signal of said ultrasonic probe means.

* * * * *